US009610124B2

(12) United States Patent
Mordaunt et al.

(10) Patent No.: US 9,610,124 B2
(45) Date of Patent: Apr. 4, 2017

(54) MEDICAL LASER WITH ELECTRONIC SHUTTER

(75) Inventors: David H Mordaunt, Los Gatos, CA (US); Charles M East, Farmington, UT (US)

(73) Assignee: Precision Medical Optics, LLC, Los Gatos, CA (US)

( * ) Notice: Subject to any disclaimer, the term of this patent is extended or adjusted under 35 U.S.C. 154(b) by 0 days.

(21) Appl. No.: 13/429,325

(22) Filed: Mar. 24, 2012

(65) Prior Publication Data

US 2012/0245571 A1    Sep. 27, 2012

Related U.S. Application Data

(60) Provisional application No. 61/465,884, filed on Mar. 25, 2011.

(51) Int. Cl.
| | |
|---|---|
| *A61B 18/20* | (2006.01) |
| *A61F 9/011* | (2006.01) |
| *H01S 5/00* | (2006.01) |
| *H01S 5/06* | (2006.01) |
| *H01S 5/068* | (2006.01) |
| *A61B 18/00* | (2006.01) |
| *A61F 9/008* | (2006.01) |
| *H01S 5/0683* | (2006.01) |

(52) U.S. Cl.
CPC ............ *A61B 18/20* (2013.01); *H01S 5/0014* (2013.01); *H01S 5/0617* (2013.01); *H01S 5/06808* (2013.01); *H01S 5/06825* (2013.01); *A61B 2018/00702* (2013.01); *A61F 9/008* (2013.01); *H01S 5/0683* (2013.01)

(58) Field of Classification Search
CPC ........... A61B 18/20; A61B 2008/00702; A61F 9/008; H01S 5/0014; H01S 5/0617; H01S 5/06808; H01S 5/06825; H01S 5/0683
USPC ............................................................. 606/4
See application file for complete search history.

(56) References Cited

U.S. PATENT DOCUMENTS

| | | | | |
|---|---|---|---|---|
| 5,736,881 | A | * | 4/1998 | Ortiz ....................... H01S 5/042 323/269 |
| 5,991,317 | A | | 11/1999 | Nighan et al. |
| 6,350,263 | B1 | | 2/2002 | Wetzig et al. |

(Continued)

FOREIGN PATENT DOCUMENTS

| | | |
|---|---|---|
| EP | 0187853 | 3/1990 |
| EP | 0425309 | 5/1991 |
| EP | 425309 A2 * | 5/1991 |

*Primary Examiner* — Gary Jackson
*Assistant Examiner* — Boniface N Nganga
(74) *Attorney, Agent, or Firm* — John E. Thomas

(57) ABSTRACT

A medical laser using solely an electronic shutter circuit for controlling the laser output, without any mechanical shutter mechanism, is provided for use in clinical applications. The medical laser has several advantages compared to medical lasers with mechanical shutters. These advantages can be defined in terms of the speed of the electronic shutter, increased reliability, increased safety, smaller and less expense. The medical laser according to the invention will shut the laser down in less than 100 microseconds making it far superior to what would be possible with a typical mechanical shutter which would take at least 10 ms to disable the laser. Safety and reliability is a result of an electronic shutter circuit with at least two current sensors, at least two photodetectors and a set of one, two or three fast electronic safety switches.

10 Claims, 3 Drawing Sheets

(56) References Cited

U.S. PATENT DOCUMENTS

| | | |
|---|---|---|
| 7,005,859 B2 * | 2/2006 | Knecht .................... 324/522 |
| 7,771,417 B2 | 8/2010 | Telfair et al. |
| 7,781,941 B2 | 8/2010 | Horvath et al. |
| 2002/0111610 A1 * | 8/2002 | Nordquist ............ A61N 5/0616 606/11 |
| 2006/0264918 A1 * | 11/2006 | Cook .................... A61B 18/22 606/10 |
| 2007/0043339 A1 | 2/2007 | Horvath et al. |
| 2007/0213693 A1 | 9/2007 | Plunkett |
| 2007/0219430 A1 | 9/2007 | Moore |
| 2009/0204109 A1 * | 8/2009 | Grove ................ A61B 18/203 606/9 |
| 2010/0145319 A1 | 6/2010 | Zimare et al. |
| 2010/0145320 A1 | 6/2010 | Horvath et al. |

\* cited by examiner

MEDICAL LASER WITH ELECTRONIC SHUTTER

CROSS-REFERENCE TO RELATED APPLICATIONS

This application claims priority from U.S. Provisional Patent Application 61/465,884 filed Mar. 25, 2011, which is incorporated herein by reference.

FIELD OF THE INVENTION

The invention relates to medical lasers. In particular, the invention relates to lasers with electronic shutters to safely deliver laser energy for medical applications.

BACKGROUND OF THE INVENTION

Medical lasers should be designed to meet safety standards to mitigate primarily against, for example, inadvertent laser exposure to body parts, over exposure with the laser treatment and single component failure. To achieve these safety standards the currently accepted standard is to utilize an electronically controlled mechanical shutter and photodetectors to deliver the laser output as shown in FIG. 1.

Mechanical shutters have proven to be slow and potentially unreliable. The mechanism of action for a mechanical shutter it to control movement and maintain a mechanical obstacle in and out of the laser beam path to prevent treatment laser light being delivered to the treatment region or even existing the laser enclosure within the device, until appropriate conditions are achieved for laser delivery. At turn-on of the device the mechanical shutter is initially "closed" (or moved into the closed position), blocking the laser output beam. Upon appropriate conditions the shutter is moved from the "closed-to-open" position, and maintained in the "open" position to allow laser delivery and treatment. Upon a second set of conditions the shutter is moved from the "open-to-closed" position, and maintained in the closed position to prevent laser delivery and treatment. Some mechanical shutters include a laser absorber to absorb the laser energy and/or a reflector to redirect the laser energy from the laser beam path to a beam dump.

The movement from "open-to-closed" (or visa versa) is usually on the order of at least tens of milliseconds as a result of the movement of mass from a stationary position to a different stationary position and accounting for acceleration, deceleration and "de-bouncing", coming to rest in the secondary stationary position. Position sensors are typically required to confirm the shutter is in an "open", "closed" or "transition" state, and often redundancy is built around the sensor and/or the shutter itself. Mechanical shutters are based on moving parts and as such subject to wear and tear and potentially sticking in either the "closed" and even more dangerous the "open" positions, resulting in an error conditions and device failures.

A typical traditional system performs a test of safety mitigations at start-up of the device with the mechanical shutter in a "closed" position, blocking external laser exposure. Such a test involves the operation of laser emission, the operation of photodetectors and test of the calibration data. In normal operation, when the user does not intend to use the laser device, the system is in Standby Mode and the mechanical shutter is closed preventing inadvertent exposure. When the user desires that the laser may be used, the user selects the Ready Mode and the mechanical shutter is opened. The user can then activate the laser emission by depressing the Laser Activation Switch.

Photodetector signals are monitored by a Safety Monitor Circuit to manage over power traditional medical laser systems. If over power is detected by the Safety Monitor Circuit, the mechanical shutter will be closed. Again, the time scale to stop this over power situation is at least tens of milliseconds, and hence is one of the weaknesses of using mechanical shutters.

To mitigate single component failure in traditional medical laser a duplication of power monitoring and safety circuits is used. Accordingly, traditional medical lasers have redundant photodetectors, internal switches in the Laser Activation Switch and redundancy on the mechanical shutter and/or sensors within.

The design of medical lasers has evolved from high voltage systems to drive gas lasers and arc lamps to pump the laser material, to high current diodes for direct laser emission and/or to pump laser material. Coming from a high voltage origin, where current sensors are not used and switching in the main electrical path are not encouraged, safety mitigations were put in place such as the mechanical shutter to block the laser light, and primary safety monitoring was done with photodetectors to monitoring the laser light directly. In particular, the mechanical shutter and photodetectors have persisted with time and through the evolution of medical laser designs, further the additional cost, design complexity and safety monitoring have previously precluded the need to build further redundancy and the concept of removing the mechanical shutter has not been implemented to date.

An alternative to a mechanical shutter is an optical shutter (for example a Pockels Cells). Rather than moving a mechanical object into the beam path to control the transmission of laser energy, an optical component is placed in the beam path which have the ability to switch from optically opaque to optically transparent. Optically opaque is analogous to a "closed" shutter position in case of a mechanical shutter blocking the laser treatment beam and optically transparent, is analogous to an "open" shutter position in case of a mechanical shutter, allowing the laser energy to be delivery to the treatment region. Optical shutters are typically expensive and have the potential of being damaged at the laser power levels utilized for medical treatments and as such are not utilized in medical laser devices.

Accordingly, there is a need in the art to develop new techniques other than mechanical or optical shutters for monitoring and safely controlling the laser output during medical laser treatments. The focus of the present invention is a medical laser device that utilizes an electronic shutter and does not include a mechanical or an optical shutter.

SUMMARY OF THE INVENTION

A medical laser using solely an electronic shutter circuit for controlling the laser output, without any mechanical shutter mechanism, is provided for use in clinical applications. A laser source (e.g. an ophthalmic laser, a diode pump solid state laser photocoagulator, or the like) powered by a laser power supply delivers a laser output. An electronic shutter circuit monitors and safely controls the laser output. The electronic shutter circuit is based on a safety monitor circuit, at least two current sensors, at least two photodetectors, and a set of electronic safety switches independent from the laser power supply. The set of switches is a set of one, two or three electronic safety switches. In one embodiment, the electronic shutter circuit has a first current sensor and a second current sensor. The first current sensor and the second current sensor both yet independently provide input to the safety monitor circuit, and the second current sensor provides input to the laser power supply. The electronic shutter circuit further has a first photodetector and a second photodetector. The first photodetector and the second photodetector both yet independently provide input to the safety monitor circuit and both sample the treatment laser beam. The electronic safety current switches are: (i) a high-voltage-side current switch, (ii) a low-voltage-side return current switch, or (iii) a shunt current switch across the laser source. The switches have a switch response time on order of 0.1 ms to 0.005 ms for clinical applications. In another example, the electronic safety current switches are: (i) a first electronic current safety switch receiving input from the laser power supply and providing input to the laser source, (ii) a second electronic current switch receiving input from the laser source and providing return path to the laser power supply, or (iii) a third electronic current switch across the laser source receiving input either directly from the laser power supply or indirectly from the laser power supply via the second electronic current switch. The safety monitor circuit could provide input to an electronic safety current switch, whereby the electronic safety current switch is independent from the laser power supply.

The medical laser with an electronic shutter according to the invention has several advantages compared to medical lasers with mechanical shutters. These advantages can be defined in terms of the speed of the electronic shutter, increased reliability, increased safety, smaller, and less expense. The medical laser according to the present invention will shut the laser down in less than 100 microseconds making it far superior to what would be possible with a typical mechanical shutter which would take at least 10 ms to disable the laser. Safety and reliability is a result of an electronic shutter circuit with at least two current sensors, at least two photodetectors and a set of one, two or three fast electronic safety switches. Such a design may also be used in the device for calibration data and also internally within the laser activation switch multiple switches to ensure—one switch held high and one switch held low, i.e. the high-voltage-side switch requires an active low control signal to activate while the shunt and low-voltage-side switches require active high signals to activate.

Applications of embodiments of the invention can generally be found in the medical field where lasers are used for treatment with emphasis on ocular conditions, laser treatment of diabetic retinopathy, and retina breaks and tears.

DETAILED DESCRIPTION

Figure 1:
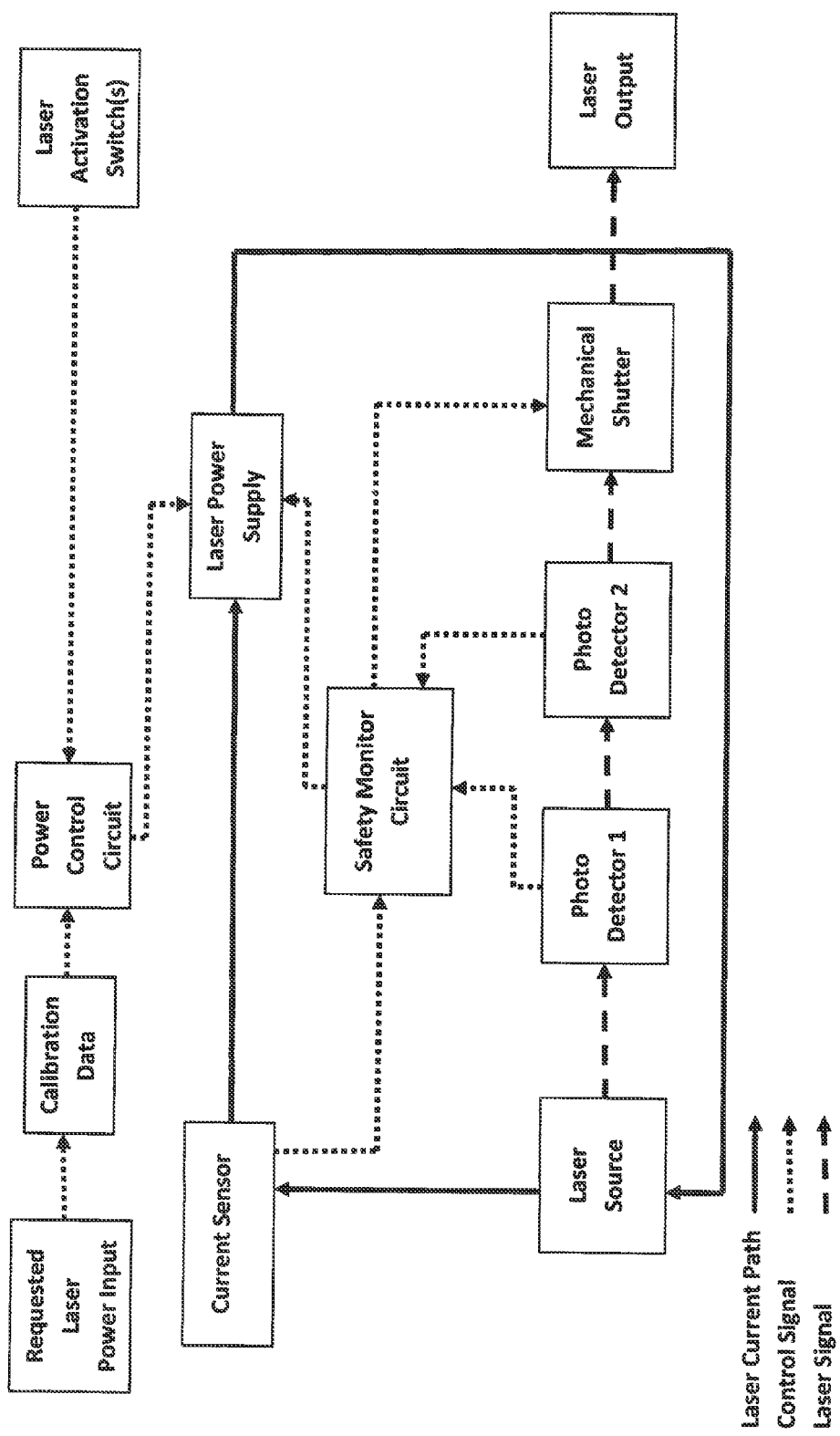
FIG. 1 shows a medical laser device using a mechanical shutter for controlling the laser output according to an example in the art.
Figure 2:
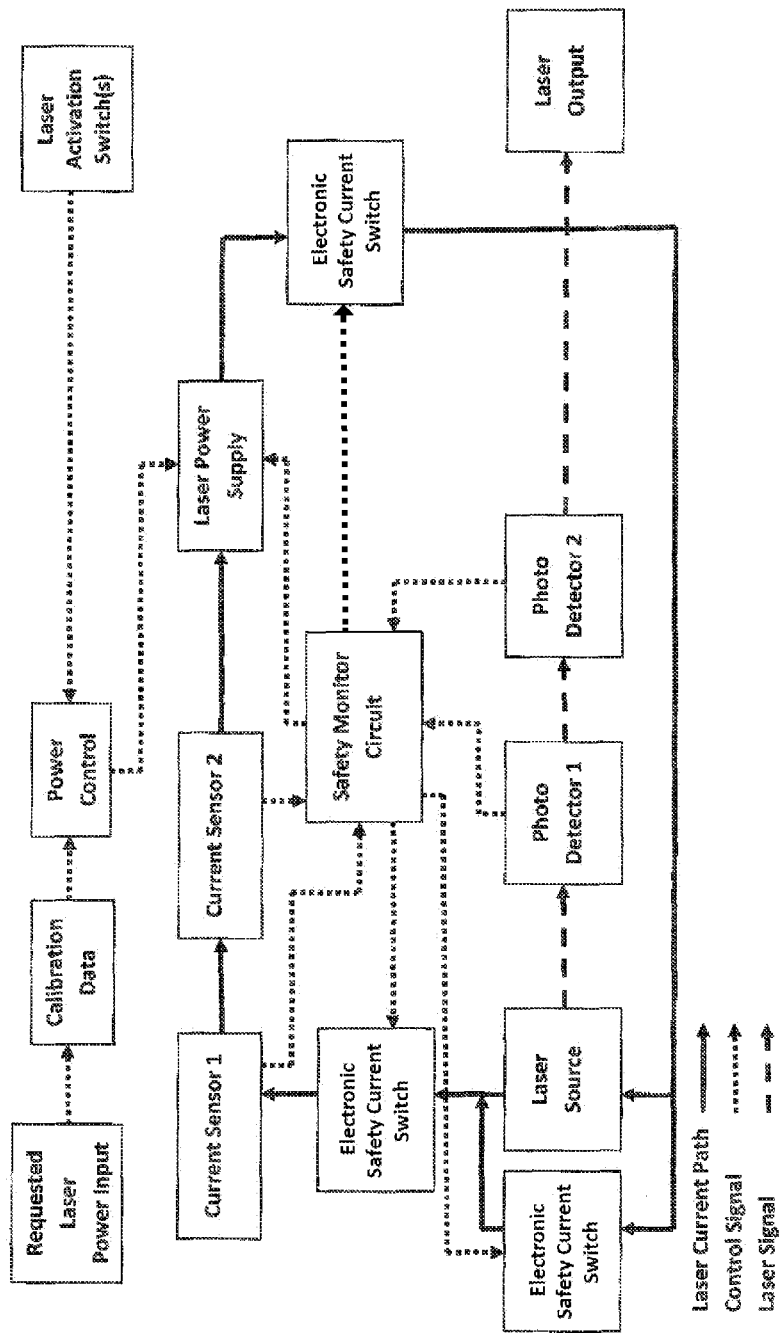
FIG. 2 shows a medical laser device using an electronic shutter according to a first exemplary embodiment of the invention.
Figure 3:
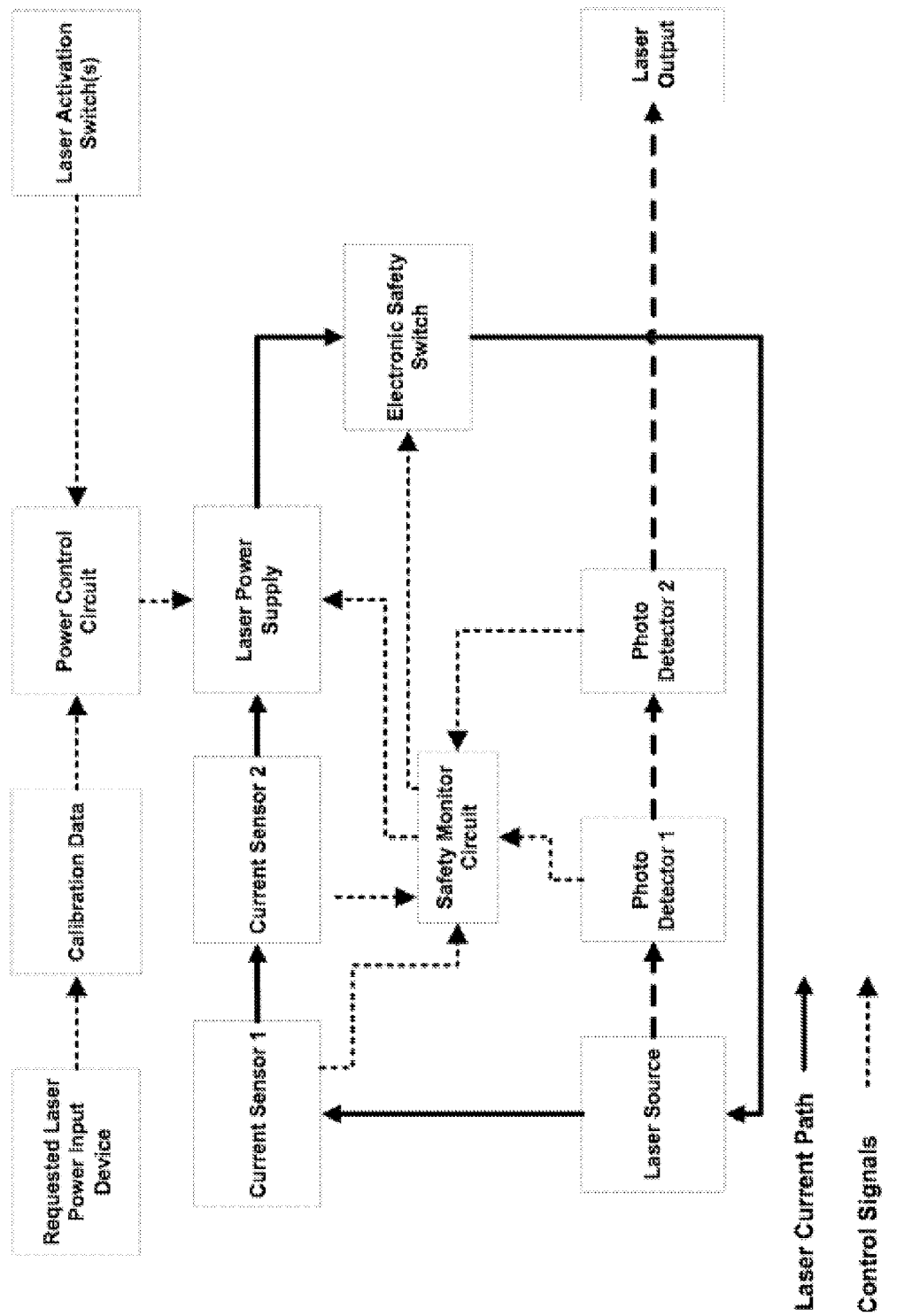
FIG. 3 shows a medical laser device using an electronic shutter according to a second exemplary embodiment of the invention.

FIGS. 2-3 shows embodiments of the invention of a medical laser with a laser source powered by the laser power supply for delivering a laser output and an electronic shutter circuit for monitoring and safely controlling the laser output. The electronic shutter circuitry entirely eliminates the need for a mechanical shutter or an optical shutter while still fulfilling the safety demands and requirement and yet even improving the safety and control of a medical laser. Thus, a medical laser of the present invention does not include any mechanical shutter mechanism for controlling the laser output.

For the active laser delivery control, the electronic shutter circuit includes at least two photodetectors, at least two current sensors, a safety monitor circuit and a set of one, two or three fast electronic switches. The current sensors and photodetectors are used in laser emission power (or energy) monitoring, its active control, and in safety controls. Safety control and power monitoring is a result of an electronic shutter circuit with at least two current sensors, at least two photodetectors and a set of one, two or three fast electronic safety switches, such that in the event of a single component failure, the device fails yet remains safe, with no laser emission.

As shown in FIGS. 2-3, at least two current sensors monitor current flow through the electronic shutter circuit to prevent a single point failure as this is now a critical function. A first current sensor is used to control current at the commanded level. A second current sensor is monitored to assure the current is well below the lasing threshold while idling. If the current exceeds the inadvertent detection threshold current the device disables current flow with a set of one, two or three fast (i.e. on order of 0.1 ms to 0.005 ms, and for no clinical effect the switch could be as slow as about 1 ms) electronic safety switches before lasing can occur. The switches in each set can be a high-side current switch, a low-side return current switch, a shunt current switch, or any combination thereof. FIG. 2 shows two electronic safety switches and a shunt safety switch. Electron current flow from negative to positive indicated by the arrows in FIGS. 2-3. High-side is regarded as being on the positive voltage side of the laser source and vice versa for the low-side. FIG. 3 shows one electronic safety switch, which is a low-side switch. The electronic high-side current switch has control of the switching power supply that provides current flow through the laser source, and thus laser emission from the laser source. To control laser delivery, this switch has the function of enabling or disable the high side current from the power supply. The electronic low-side return current switch has control to enable or disable the direct connection from low-side of the laser source thus actively controlling the current flow and thus laser emission of the laser source.

The electronic shunt (short-circuit) current switch shorts across the laser source shunting any current that would otherwise conduct through the laser source directly to ground thus disabling laser emission.

As shown in FIGS. 2-3, at least photodetectors monitor the laser emission power (or energy). These photodetectors are used to prevent a single point failure. According to the embodiments of FIGS. 2-3, a first photodetector is used to control the laser source current via the power control circuit. A second photodetector is used to compare its output against a secondary reference and is verified to be within a predetermined safety window (i.e. typically secondary measurement need to be within 50 to 150% of the redundant reference). If the measurement from the second photodetector is outside this predetermined safety window, a safety error is flagged in the Safety Monitor Circuit and the medical laser device disables laser emission with a set of one, two or three fast electronic switches before lasing can occur. The switches in each set, as described supra, can be a high-side current switch, a low-side return current switch, a shunt current switch, or any combination thereof.

In the medical laser device, without a mechanical shutter, laser emission would not be internally contained within the device. So to mitigate the potential of inadvertent laser exposure, the devices utilizes at least 3 states of the device: Standby, Ready and Treat modes.

1. Standby—the device is in the Standby mode, by default. In this mode the electronic shutter prevents laser emission (i.e. where applicable the high-side, low-side switches are open and the shunt switch is closed). No electrical current can flow through the laser source, thus laser emission cannot occur.

2. Ready—the user has to actively select the transition to this mode. At this point, the electronic shutter prepares the switches, where applicable, such that electrical can flow through the laser source. Typically the laser source has current passing through it below the threshold for laser emission, at the predetermined idle current (monitored by the current sensors). The laser source does not emit in this mode, but is ready to emit. Safety mitigations are active, i.e. current sensors and photodetectors monitoring current is below the threshold for laser emission and no laser emission is detected with the photodetectors.

Inadvertent laser exposure can be mitigated according to the following example. If there is a failure in the first current sensor, the current will rise uncontrolled until it hits 5 amps, as measured by the second current sensor. This will cause the laser to shut down the laser before any light is emitted at the lasing threshold of 10 amps or more.

3. Treat—only when the device is in the Ready mode can it transition to Treat mode. Laser emission is activated by the user selecting the Laser Activation Switch. This increases the current through the Laser Source to achieve laser emission. To achieve a user desired laser power, the request laser power supply output is calculated in the power control circuit utilizing calibration data, this request is sent to the laser power supply and the current increases through laser source. As the current increases above the laser current threshold, laser emission occurs. There are two photodetectors that sample the main laser emission beam. The photodetectors measure the laser light emitted. One photodetector is used in a closed loop iteration to adjust the laser power supply output such that the desired laser emission level is reached. The second photodetector is compared to the first photodetector to ensure that they are consistent.

By idling the laser before generating a laser output and monitoring with a redundant current sensor, one can now identify many failures in the laser power supply that may cause a situation where the laser would fire uncontrolled before the laser is allowed to fire. In addition, there is an added benefit of extending the laser diode life, by not shutting it all the way off between pulses.

Variations and Additional Embodiments

Three independent shutdown methods can be used to insure the laser is disabled and cannot have an unintended exposure event. The first shutdown is direct control of the laser power supply that provides current to the laser diode to fire the laser. This control will disable the internal switching element(s) (such as a FET, IGBT, BJT) used to provide current to the laser. The second shutdown can be an electronic switch external to the laser power supply such that provides the return path for the laser diode. This switching element will be disabled whenever an error condition occurs or when the laser is in any mode where current should not be flowing through the laser diode. The third method can be a switching element that provides a shunt (short circuit) in parallel with the laser diode. This switching element will be enabled whenever an error condition occurs or when the laser is in any mode where current should not be flowing through the laser diode.

When a laser power supply shutdown occurs three independent circuits can be utilized to immediately disable the laser output. The first circuit disables the switching elements that source current to the laser diode. The second circuit disables the switching element that sinks current from the laser diode. The third circuit shorts a switching element across the output of the laser power supply assuring no current can conduct through the laser diode.

To further assure power output level is correct the system compares the primary and secondary power control signals with a hardware comparator, if the primary and secondary control signals are not within 10% of each other the power supply is disabled and the laser cannot be fired.

Further embodiments, variations or teachings can be found in U.S. Provisional Patent Application 61/465,884 filed Mar. 25, 2011, which is incorporated herein by reference in its entirety.

What is claimed is:

1. A medical laser having a standby mode, a ready mode, and a treatment mode, the medical laser comprising:
   (a) a laser source for delivering a laser output, wherein said laser source receives, from a laser power supply, no current in said standby mode, a current passing through said laser source at an idle level that does not cause said laser source to emit said laser output in said ready mode, and the current at a commanded level that causes said laser source to emit said laser output in said treatment mode; and
   (b) an electronic shutter circuit for monitoring and safely controlling said laser output, wherein said electronic shutter circuit comprises:
   (i) a safety monitor circuit;
   (ii) a first current sensor and a second current sensor, wherein said first current sensor and said second current sensor each independently provide input to said safety monitor circuit, and wherein said first current sensor controls the current at said commanded level while the medical laser is in said treatment mode, and wherein said second current sensor provides input to disable current flow through said laser power supply if the current exceeds a threshold current while the medical laser is in said ready mode;
   (iii) a first electronic safety current switch receiving input from said safety monitor circuit and being independent from said laser power supply, said first electronic safety current switch being coupled in parallel with said laser source as a shunt across said laser source; and
   (iv) a first photodetector and a second photodetector that each monitor an emission power of said laser output and provide an input to said safety monitor circuit;
   wherein the medical laser does not include a mechanical shutter mechanism for controlling said laser output.

2. The medical laser as set forth in claim 1 further comprising:
   a high-voltage-side current switch; and
   a low-voltage-side return current switch.

3. The medical laser as set forth in claim 1, further comprising:
   a second electronic safety current switch receiving input from said laser power supply and providing input to said laser source; and a third electronic safety current switch receiving input from said laser source and providing return path to said laser power supply.

4. The medical laser as set forth in claim 1, wherein said laser source is an ophthalmic laser.

5. The medical laser as set forth in claim 1, wherein said laser source is a diode pump solid state laser photocoagulator.

6. The medical laser as set forth in claim 1 further comprising:
a high-voltage-side current switch.

7. The medical laser as set forth in claim 1 further comprising:
a low-voltage-side return current switch.

8. The medical laser of claim 1,
wherein said first photodetector provides a first output to said safety monitor circuit based on the emission power, said safety monitor circuit controlling the current provided from said laser power supply to said laser source based on the first output, and
said second photodetector provides a second output to said safety monitor circuit based on the emission power independently of the first photodetector, said safety monitor circuit disabling said laser output if said second output indicates said laser output is outside a predetermined safety window.

9. The medical laser of claim 1 wherein the medical laser only transitions to said treatment mode if the medical laser is in said ready mode so that said safety monitor circuit can identify failures in said laser power supply based on the current exceeding the threshold current while the medical laser is in said ready mode prior to operating said laser source at said commanded level.

10. The medical laser of claim 9 wherein the medical laser only transitions from said treatment mode to said ready mode so that said laser source is not shut all the way off between pulses.

* * * * *